United States Patent [19]

Okumoto et al.

[11] Patent Number: 5,104,220

[45] Date of Patent: Apr. 14, 1992

[54] ATOMIC ABSORPTION SPECTROPHOTOMETER AND ANALYZING METHOD

[75] Inventors: Toyoharu Okumoto; Katsuhito Harada, both of Katsuta; Konosuke Oishi, Mito, all of Japan

[73] Assignee: Hitachi, Ltd., Tokyo, Japan

[21] Appl. No.: 316,964

[22] Filed: Feb. 28, 1989

[30] Foreign Application Priority Data

Mar. 4, 1988 [JP]  Japan .................................. 63-49537

[51] Int. Cl.⁵ .......................... G01J 3/42; G01N 21/74
[52] U.S. Cl. .................................... 356/307; 356/312; 356/319
[58] Field of Search ............... 356/328, 307, 311, 326, 356/312, 36, 319

[56] References Cited

U.S. PATENT DOCUMENTS

4,008,963  2/1977  Huber et al. .
4,341,470  7/1982  Parker et al. ...................... 356/307

FOREIGN PATENT DOCUMENTS

1773571  7/1971  Fed. Rep. of Germany .
2165106  7/1972  Fed. Rep. of Germany .
2008295  5/1973  Fed. Rep. of Germany .
2410892  9/1975  Fed. Rep. of Germany .
31107783A1  2/1982  Fed. Rep. of Germany .
3202825A1  8/1982  Fed. Rep. of Germany .

OTHER PUBLICATIONS

"Backround-Corrected Simultaneous Multielement Atomic Absorption Spectrometer", Harnly et al., Analytical Chemistry, vol. 51, #12, Oct. 1979, pp. 2007-2014.

"Atomic Absorption Spectrophotometric Determination of Antimony, Arsenic, Bismuth . . . " Kempton et al., Talante, vol. 29, #8, Aug. 1982, pp. 675-681.

"Atomic-Absorption Determination of Carbide-Forming Elements . . . "L'vovetal, Kalinin Polytechnical Inst., Trans; Zavoskaya Laboratories, vol. 44, #2, Feb. 1978, pp. 173-176.

"Preliminary Investigation of the Flame Resonance Spectrometer Used in a Graphite Furnace", Loon et al., Atomic Absorption Newsletter, vol. 15, #3, May-Jun. 1976, pp. 61-63.

"A Multichannel Spectrometer for Simultaneous Atomic Absorption and Flame Analysis", Mavrodineau et al., Applied Optics, vol. 7, #7, Jul. ·68, pp. 1281-1285.

"Simultaneous Determination of Manganese, Colbalt, and Copper with Computer Controlled . . . " Lundberg et al., Analytical Chemistry, vol. 48, #13, Nov. 1976, pp. 1922-1926.

"New Directions in Optical Atomic Spectrometry," Galan, Analytical Chemistry, vol. 58, #6, May 1986, pp. 697A-707A.

*Primary Examiner*—F. L. Evans
*Assistant Examiner*—K. P. Hantis
*Attorney, Agent, or Firm*—Antonelli, Terry, Stout & Kraus

[57] ABSTRACT

An atomic absorption spectrophotometer comprising means for setting the ashing temperature for that of the element having the lowest ashing temperature; means for setting the atomizing temperature for that of the element having the highest atomizing temperature; and means for effecting background correction utilizing Zeeman effect.

5 Claims, 4 Drawing Sheets

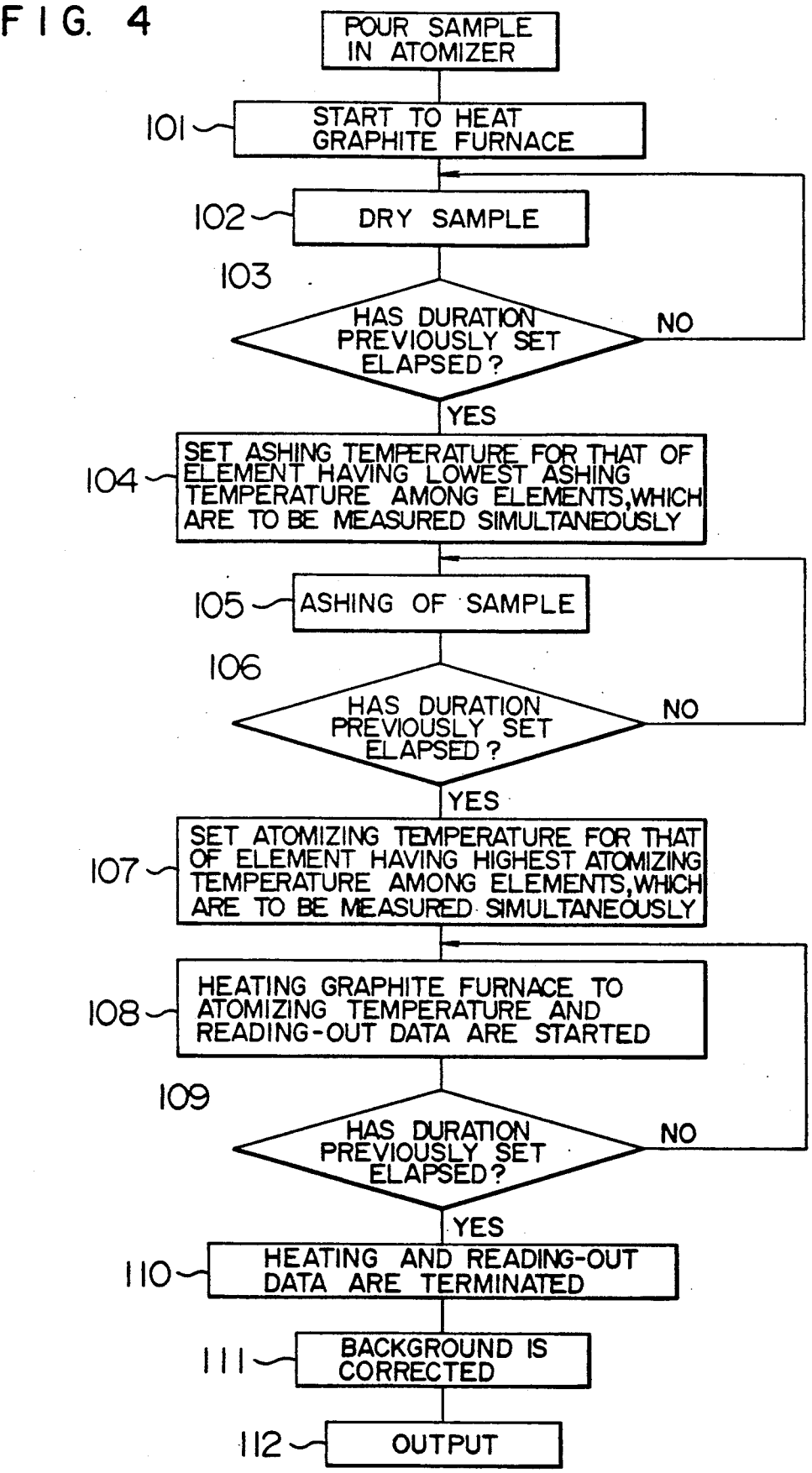

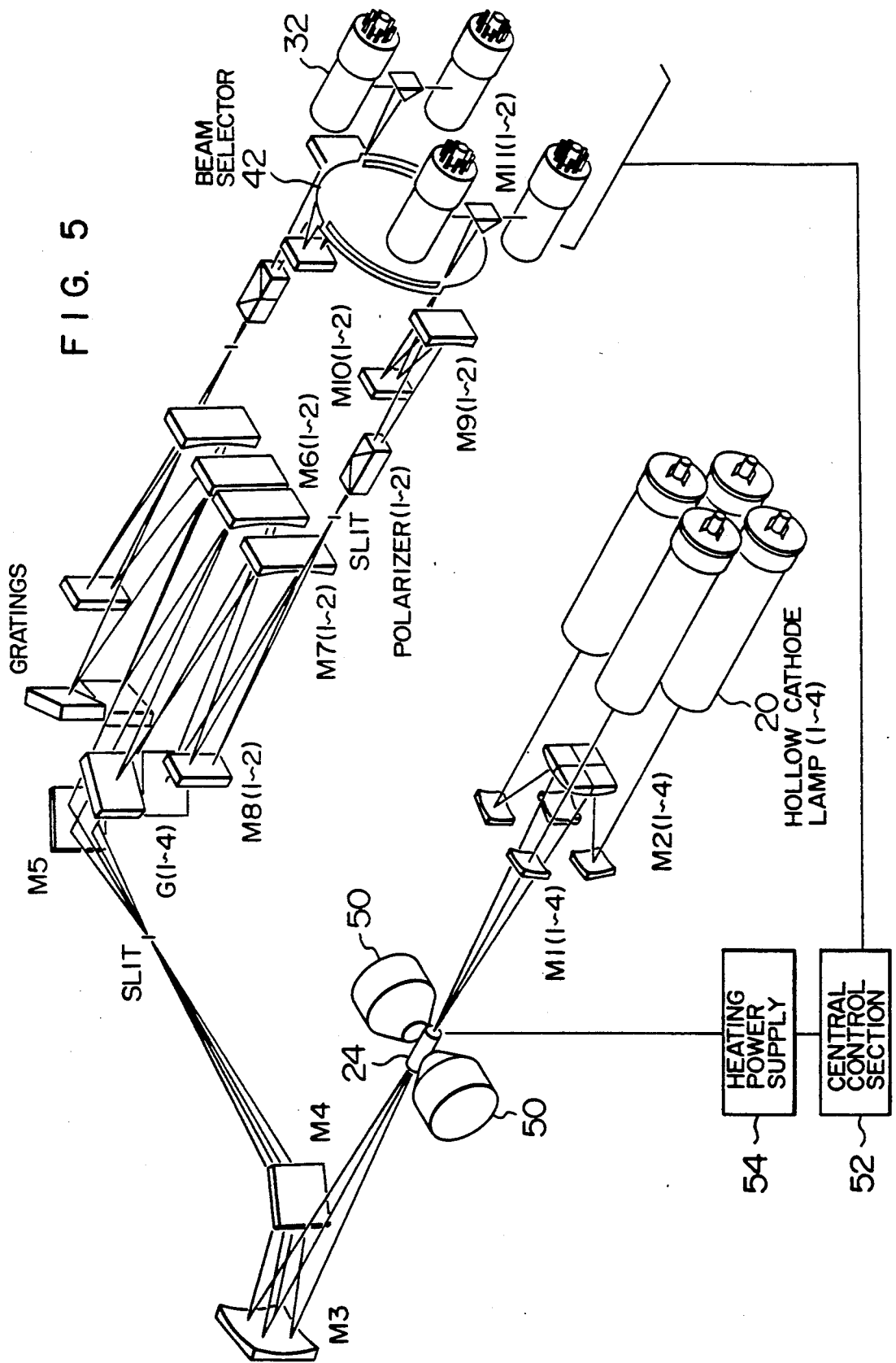

ATOMIC ABSORPTION SPECTROPHOTOMETER AND ANALYZING METHOD

BACKGROUND OF THE INVENTION

This invention relates to an atomic absorption spectrophotometer, and in particular to an atomic absorption spectrophotometer and an analyzing method therewith, which are suitable for quantitatively analyzing simultaneously a plurality of metallic elements of small quantity, which are resolved in an aqueous solution.

An atomic absorption spectrophotometer using a graphite furnace has different programs concerning the ashing temperature and the atomizing temperature for different elements, which are objects to be measured, and effects quantitative analysis of the elements, which are objects to be measured, by transforming a sample to be measured into atomic vapor by heating the graphite furnace according to these temperature programs and by measuring the degree of light absorption while making light coming from a light source pass through this atomic vapor.

For an atomic absorption spectrophotometry using a graphite furnace an optimum temperature program is determined for every element, which is an object to be measured, taking the magnitude of the absorption sensitivity, the reliability, the life of the cuvette, etc. into account. The ashing temperature and the atomizing temperature according to this temperature program are determined, taking the following items into account.

i) Ashing temperature

The ashing temperature is a temperature set as high as possible as far as the aimed element is not atomized at this ashing step. When this temperature is too low, ashing is insufficient; components other than the aimed element remain; and background absorption at the atomizing step is increased, which reduces the reproducibility. On the other hand, when the ashing temperature is too high, the element to be measured is vaporized at the atomizing step. For this reason absorption peaks at the atomizing step become smaller, which reduces the sensitivity. As explained above, it is necessary to set the ashing temperature as high as possible as far as the aimed element is not vaporized at the ashing step.

ii) Atomizing temperature

The atomizing temperature is a temperature set sufficiently high for obtaining the greatest absorption of light having a specified wavelength due to the aimed element at the atomizing step. This is because the aimed element is not sufficiently atomized, which reduces the sensitivity, if the atomizing temperature is too low. For example for cadmium, which is a low melting point element, the ashing temperature is about 300° C. and the atomizing temperature is about 1500° C. On the other hand, for vanadium, which is a high melting point element measurements are effected with a temperature program, by which the ashing temperature is about 900° C. and the atomizing temperature is about 3000° C.

As described above, by the atomizing absorption spectrophotometry using a graphite furnace, since the optimum temperature program, i.e. ashing and atomizing temperatures, are determined for every element, heretofore measurement is effected for every single element.

As techniques relating to this invention, a method for obtaining the optimum ashing temperature and the optimum atomizing temperature is disclosed in JP-A-58-37540 (filed on Aug. 29, 1981 by Sumitomo Electric Industries, Ltd., Inventor: Masahiro Shibata). Further techniques for arranging a plurality of light sources at predetermined positions are disclosed in JP-A-63-292040.

SUMMARY OF THE INVENTION

The object of this invention is to provide an atomic absorption spectrophotometer and an analyzing method therewith capable of effecting analysis of a plurality of elements simultaneously by one measurement and with a high efficiency.

In order to achieve this object, according to this invention, ashing as an intermediate treatment is effected by setting the ashing temperature for that of the element having the lowest ashing temperature among the plurality of elements, while atomizing at the step of taking-in data is effected by setting the atomizing temperature for that of the element having the highest atomizing temperature among the plurality of elements or the highest temperature of the atomizing device itself, and at the same time influences of impurities at the atomizing step are removed by means of background correcting means.

The ashing temperature is set as high as possible as far as the aimed element to be measured is not atomized, for the purpose of removing impurities other than the aimed elements at the ashing step. Consequently, in the case where measurements of a plurality of elements are effected simultaneously, the ashing temperature is set for that of the element having the lowest ashing temperature among the elements measured simultaneously. When the ashing temperature is low, ashing is insufficient and background absorption at the atomizing step is great, which reduces the reproducibility. For this reason, since background correction can be effected at the atomizing step by using a device provided with a background correcting function, e.g. by Zeeman effect, it is possible to set the ashing temperature for a low value.

The atomizing temperature should be set for a temperature, at which the aimed element to be measured is sufficiently atomized. If the atomizing temperature were too low, the aimed element would not be sufficiently atomized, which would reduce the sensitivity. Consequently, in the case where a plurality of elements are measured simultaneously, by setting the atomizing temperature for that of the element having the highest atomizing temperature among a plurality of elements, which are to be measured simultaneously, or the highest temperature of the atomizing device itself, all the elements to be measured are atomized one after another with increasing ashing temperature and in this way simultaneous measurements of a plurality of elements are possible.

As explained above, according to this invention, simultaneous measurements of a plurality of elements having different temperature programs, i.e. different ashing and atomizing temperatures, are possible and thus it is possible to try to shorten remarkably measurement time and to reduce the amount of the sample for the atomic absorption spectrophotometry.

BRIEF DESCRIPTION OF THE DRAWINGS

FIG. 4 is a flow chart of the temperature program according to this invention; and FIG. 5 illustrates an embodiment, in the case where the number of sorts of elements to be analyzed is four.

DESCRIPTION OF THE PREFERRED EMBODIMENTS

Hereinbelow an embodiment of the atomic absorption spectrophotometer according to this invention will be explained.

Figure 1:
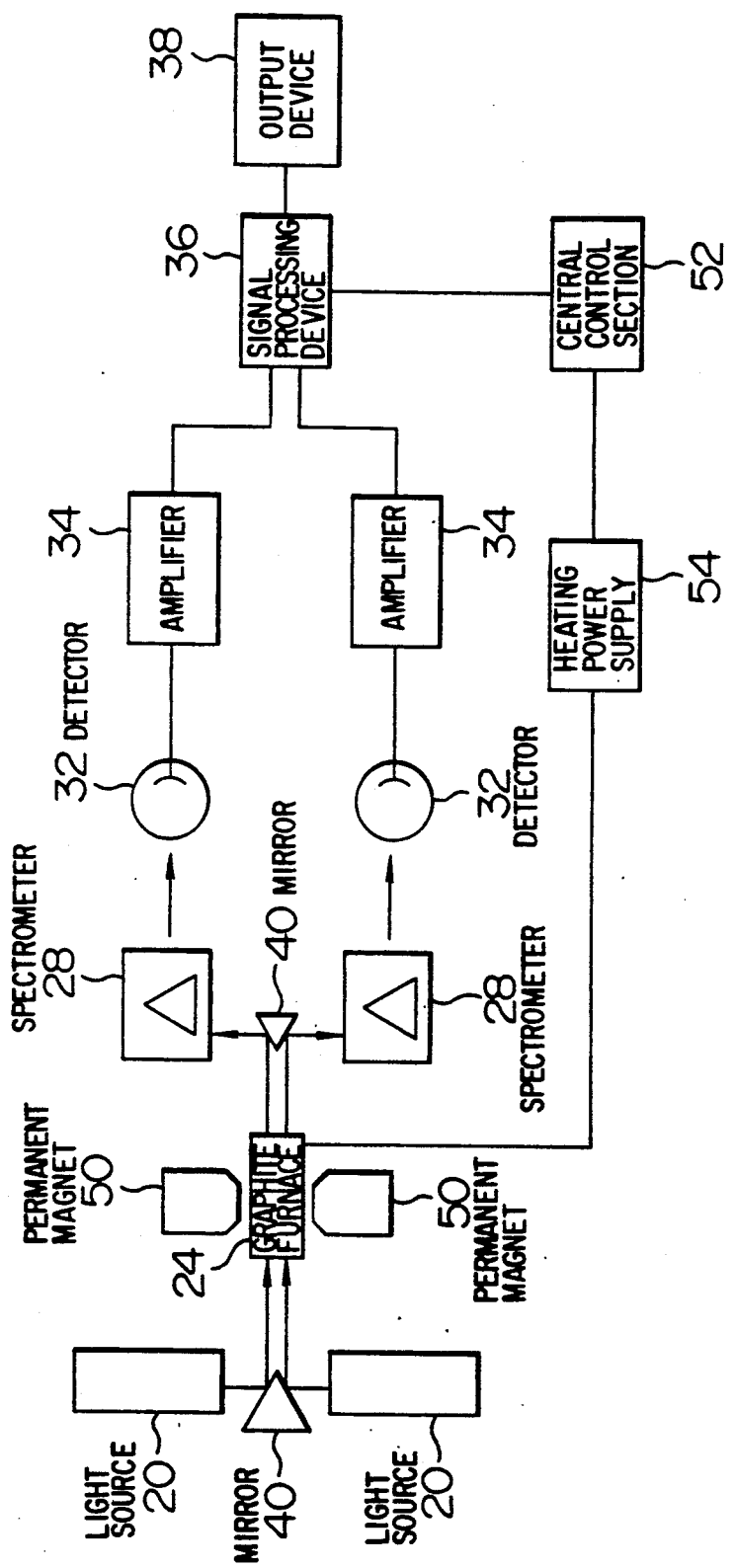
FIG. 1 is a block diagram illustrating the construction of an atomic absorption spectrophotometer according to this invention.
Figure 2:
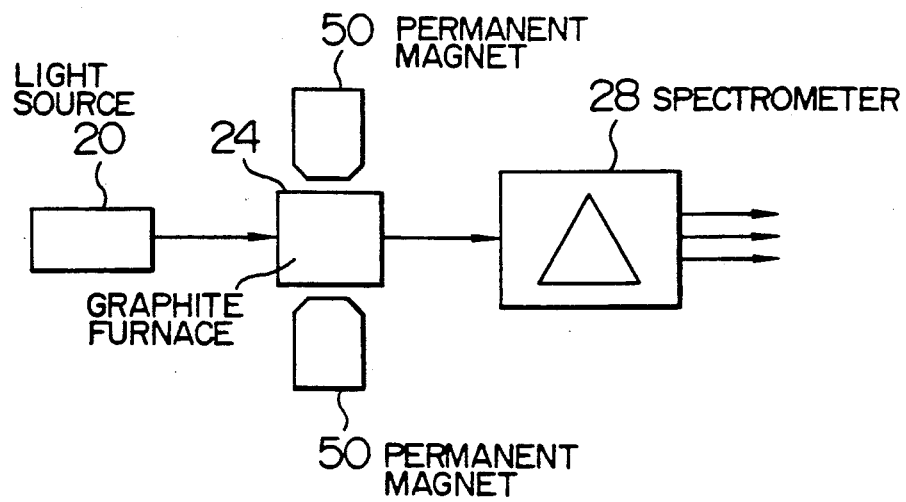
FIG. 2 is a scheme illustrating an embodiment for taking out a plurality of wavelengths to be analyzed from a spectrometer.

In FIG. 1, a sample, in which a plurality of elements to be analyzed are dissolved, is poured in a graphite furnace 24. The sample is heated by Joule heat generated by electric power supplied by a heating power supply 54 to the graphite furnace and transformed into atomic vapor. At this time background, i.e. influences of components other than the aimed elements are removed by utilizing so-called Zeeman effect, by which atomic absorption lines are split by a permanent magnet 50. The correction utilizing Zeeman effect is explained in detail in HITACHI TECHNICAL DATA AA, SHEET No. 19, SECTION 2.1. Light flux from a plurality of light sources 20 emitting light corresponding to a plurality of elements to be analyzed are made to pass through this atomic vapor. Light beams having analysis wavelengths are selected by a plurality of spectrometers 28, each of which is set for each of the analysis wavelengths and light beams thus selected are injected in detectors 32. The light beams injected in the detectors 32 are transformed into electric signals, which are amplified by amplifiers. Thereafter they are treated by a single processing device 36 and a value of the quantitative analysis is obtained for every aimed element and outputted to an output device 38. Reference numeral 40 represents a mirror. The signal processing device 36 and the heating power supply 54 are controlled by a predetermined program by means of a central control section 52 including a CPU and memories. As the light source, either a single light source such as a composite lamp, etc., in which the light emitting source consists of a plurality of metals, capable of emitting light having different analysis wavelengths of a plurality of elements may be used, or a plurality of analysis wavelengths to be detected may be taken out from one spectrometer 28, as indicated in FIG. 2.

Figure 3:
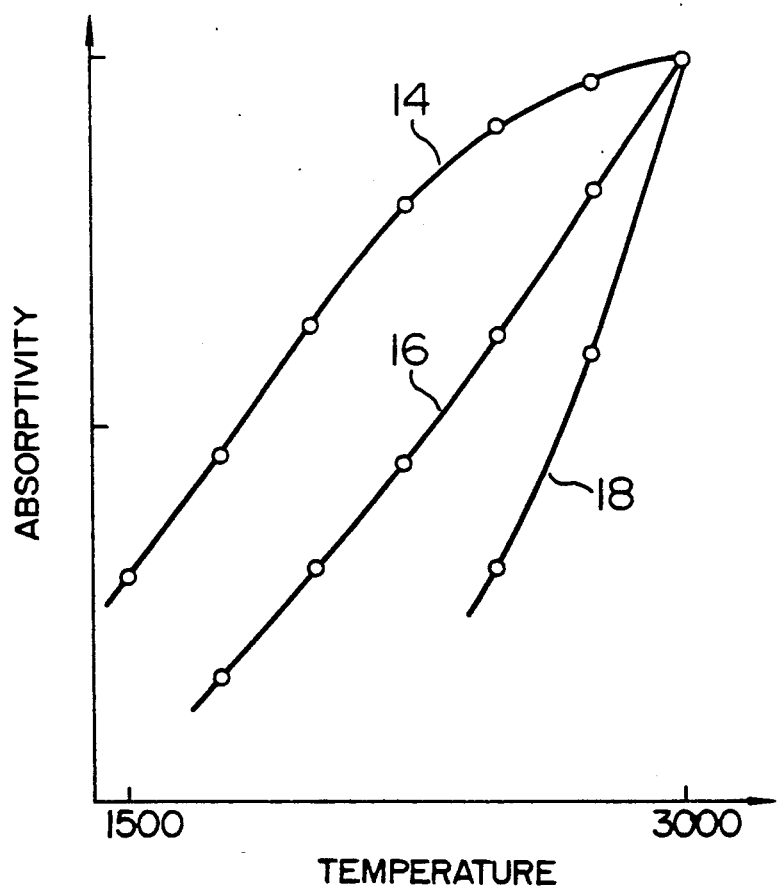
FIG. 3 is a graph showing the relation between the atomizing temperature and the light absorptivity for a plurality of elements.

FIG. 3 shows variations in the absorptivity, when three elements having different melting points are measured simultaneously by using the same temperature program.

It shows data obtained, when the common ashing temperature is set for 300° C. and the atomizing temperature for 3000° C., using cadmium (ashing temperature: 300° C., atomizing temperature: 1500° C.) as a low melting point element 14; manganese (ashing temperature: 500° C., atomizing temperature: 2500° C.) as a middle melting point element 16; and vanadium (ashing temperature: 900° C., atomizing temperature; 3000° C.) as a high melting point element. As it is clearly seen from the figure, for all of these three elements, the absorptivity increases with increasing atomizing temperature. The absorptivity of the low melting point element 14 is higher than that of the high melting point element 18 and the middle melting point element 16 also for the low atomizing temperatures and its tendency that the absorptivity increases with increasing atomizing temperature is the same as that of the other. That is, for the atomizing temperature, it is shown that, when a plurality of elements having different atomizing temperatures should be analyzed simultaneously by using only one temperature program, the simultaneous measurement is possible, if the atomizing temperature of the element having the nighest atomizing temperature among the plurality of elements, which are to be measured simultaneously, is used for the other elements.

FIG. 4 shows a flow chart of the temperature program used for this embodiment.

This program is executed by the CPU and a memories in the central control section 52.

After the sample has been poured in an atomizer, heating of the graphite furnace is started in Step 101.

The sample is dried for a predetermined period of time in Steps 102 and 103.

The ashing temperature is set for that of the element having the lowest ashing temperature among the elements, which are to be measured simultaneously, in Step 104.

After having effected the ashing for a predetermined duration in Steps 105 and 106, the temperature of the furnace is raised for atomizing in Step 107. The atomizing temperature is set for that of the element having the highest atomizing temperature among the elements, which are to be measured simultaneously.

The graphite furnace is heated to the atomizing temperature in Steps 108 and 109 and data are read-out.

The heating and the reading-out of the data are terminated in Step 110; the background correction of detected signals is effected in Steps 111 and 112; and the result is outputted to the output device.

FIG. 5 illustrates another embodiment of this invention. This embodiment is an example, in which there are four elements to be analyzed. There are disposed four light sources 20, which generate light beams having specified wavelengths used for analysis of different elements to be analyzed. The light beams emitted by the light sources 20 intersect each other in a graphite furnace 24 and a spectrometer system principally composed of mirrors (M1–M11) and disposed therebehind is so constructed that light beams having the different wavelengths can be separately taken out. The light beams separated by this spectrometer system are divided into two polarized components. The detection thereof is effected by rotating a beam selector 42 so that these polarized components are alternatively selected and transmitted and by making them inject to respective detectors 32.

We claim:

1. An atomic absorption spectrometer comprising:
   light sources emitting a plurality of light beams having different wavelengths corresponding to a plurality of elements to be simultaneously analyzed;
   an atomizing furnace for ashing and atomizing said plurality of elements;
   temperature control means for controlling the temperature of said atomizing furnace so as to be the ashing temperature and the atomizing temperature suitable for said elements to be analyzed;
   spectrometric means for selecting a plurality of light beams transmitted by said plurality of elements to be analyzed;

detecting means for detecting said plurality of light beams selected by said spectrometric means;

means for effecting background correction for signals detected by said detecting means, said means for effecting background correction including means utilizing the Zeeman effect; and a signal processing device for processing said signals detected by said detecting means and corrected by said correcting means;

wherein said temperature control means includes means for setting said ashing temperature to that of the element having the lowest ashing temperature, and means for setting said atomizing temperature to that of the element having the highest atomizing temperature.

2. An atomic absorption spectrophotometer according to claim 1, wherein said atomizing furnace is a graphite furnace.

3. An atomic absorption spectrophotometer according to claim 1, wherein said spectrometric means is a spectrometer.

4. An atomic absorption spectrophotometric method for enabling simultaneous analysis of a plurality of elements utilizing a plurality of light beams having different wavelengths corresponding to the plurality of elements;

introducing the plurality of elements into a furnace for atomizing and ashing the plurality of elements;

setting a temperature of the furnace to the ashing temperature of an element which has the lowest ashing temperature among the plurality of elements to be simultaneously analyzed during an ashing phase;

setting the temperature of the furnace to the atomizing temperature of an element which has the highest atomizing temperature among the plurality of elements to be simultaneously analyzed during an atomizing phase;

transmitting the plurality of light beams through the furnace;

detecting said transmitted light beams; and effecting background correction utilizing the Zeeman effect for detected signals.

5. An atomic absorption spectrophotometric method according to claim 4, wherein the steps of setting the temperature of the furnace to the ashing temperature and the atomizing temperature includes controlling the temperature of an atomizing furnace for ashing and atomizing the plurality of elements, and effecting spectrophotometric analysis of the plurality of elements including detecting signals thereof.

* * * * *